(12) United States Patent
Saitou et al.

(10) Patent No.: US 11,433,205 B2
(45) Date of Patent: Sep. 6, 2022

(54) BREATHING APPARATUS PROVIDED WITH A BREATH-SYNCHRONIZED MOTOR FAN

(71) Applicant: SHIGEMATSU WORKS CO., LTD., Tokyo (JP)

(72) Inventors: Wataru Saitou, Saitama (JP); Kenichi Ono, Saitama (JP); Hiroyuki Ide, Saitama (JP)

(73) Assignee: SHIGEMATSU WORKS CO., LTD., Tokyo (JP)

( * ) Notice: Subject to any disclaimer, the term of this patent is extended or adjusted under 35 U.S.C. 154(b) by 286 days.

(21) Appl. No.: 16/321,122

(22) PCT Filed: Apr. 13, 2017

(86) PCT No.: PCT/JP2017/015168
§ 371 (c)(1),
(2) Date: Jan. 28, 2019

(87) PCT Pub. No.: WO2018/020753
PCT Pub. Date: Feb. 1, 2018

(65) Prior Publication Data
US 2019/0160246 A1    May 30, 2019

(30) Foreign Application Priority Data
Jul. 26, 2016 (JP) ............... JP2016-146838

(51) Int. Cl.
*A61M 16/06* (2006.01)
*A62B 18/08* (2006.01)
(Continued)

(52) U.S. Cl.
CPC ........ *A61M 16/06* (2013.01); *A61M 16/0069* (2014.02); *A61M 16/107* (2014.02);
(Continued)

(58) Field of Classification Search
CPC ............... A61M 16/00; A61M 16/06; A61M 2016/0015–0042; A62B 7/00;
(Continued)

(56) References Cited

U.S. PATENT DOCUMENTS

| 4,886,056 A * | 12/1989 | Simpson | ............... | A62B 18/006 |
| | | | | 128/201.25 |
| 7,128,069 B2 * | 10/2006 | Farrugia | ........... | A61M 16/0069 |
| | | | | 128/204.18 |
| 2010/0083967 A1 | 4/2010 | Kuriyama | | |

FOREIGN PATENT DOCUMENTS

CN  105577037 A  5/2016
EP  0 352 938 A2  1/1990
(Continued)

OTHER PUBLICATIONS

Extended European Search Report issued in co-pending application 17833764.8 completed Jul. 3, 2019 and dated Jul. 15, 2019.
(Continued)

*Primary Examiner* — Samchuan C Yao
*Assistant Examiner* — Ned T Heffner
(74) *Attorney, Agent, or Firm* — Merchant & Gould P.C.

(57) ABSTRACT

An object of the present invention is to provide a breathing apparatus, wherein current for keeping internal pressure of the face piece at a predetermined positive target value at the time of inhale is not applied to the motor fan in a large amount at the start of current application to the motor fan, and the internal pressure of the face piece is prevented from becoming far below the predetermined positive target value immediately after start of current application to the motor fan so as to keep the internal pressure of the face piece at the predetermined positive target value at the time of inhale.

A breathing apparatus provided with a breath-synchronized motor fan comprising a face piece for covering a part of or all of a face of a user, an inhale valve and an exhale valve (Continued)

attached to the face piece, a motor fan for supplying internal space of the face piece with external air through the inhale valve, a filter for cleaning the external air to be sucked into the motor fan, a breath monitoring apparatus provided with a membrane member deforming in accordance with fluctuation of internal pressure of the face piece and a sensor for detecting the deformation of the membrane member, and a controller for controlling operation of the motor fan synchronously with breathing of the user in accordance with a detection signal from the breath monitoring apparatus, wherein the controller applies current to the motor fan at the time of inhalation so as to keep the internal pressure of the face piece at a predetermined positive target value, and stops current application to the motor fan so as to stop the motor fan at the time of exhalation, and wherein the controller applies micro-current to the motor fan so as to rotate the motor fan at extremely low speed from the middle of exhalation to inhalation.

1 Claim, 3 Drawing Sheets

(51) Int. Cl.
*A62B 18/00* (2006.01)
*A61M 16/00* (2006.01)
*A61M 16/10* (2006.01)
*A61M 16/20* (2006.01)
*A62B 18/10* (2006.01)

(52) U.S. Cl.
CPC ............ *A62B 18/006* (2013.01); *A62B 18/08* (2013.01); *A61M 16/208* (2013.01); *A61M 2016/0015* (2013.01); *A61M 2205/707* (2013.01); *A61M 2205/7563* (2013.01); *A61M 2205/8212* (2013.01); *A62B 18/10* (2013.01)

(58) Field of Classification Search
CPC ....... A62B 7/02–04; A62B 7/10; A62B 9/006; A62B 9/02; A62B 9/022–027; A62B 9/04; A62B 23/00; A62B 23/02–025; A41D 13/11
See application file for complete search history.

(56) References Cited

FOREIGN PATENT DOCUMENTS

| | | |
|---|---|---|
| EP | 3 446 754 A1 | 2/2019 |
| JP | 2008-086644 A | 4/2008 |
| JP | 2009-136521 A | 6/2009 |
| JP | 2013-075157 A | 4/2013 |
| JP | 2013-220280 A | 10/2013 |
| JP | 2015-221170 A | 12/2015 |
| KR | 10-2006-0115288 A | 11/2006 |
| KR | 10-068599 B1 | 1/2007 |
| WO | 00/27021 A1 | 5/2000 |
| WO | 2013/039153 A1 | 3/2013 |

OTHER PUBLICATIONS

Written Opinion of the International Searching Authority issued in PCT/JP2017/015168 dated May 23, 2017.
International Search Report issued in PCT/JP2017/015168, completed May 11, 2017 and dated May 23, 2017.

* cited by examiner

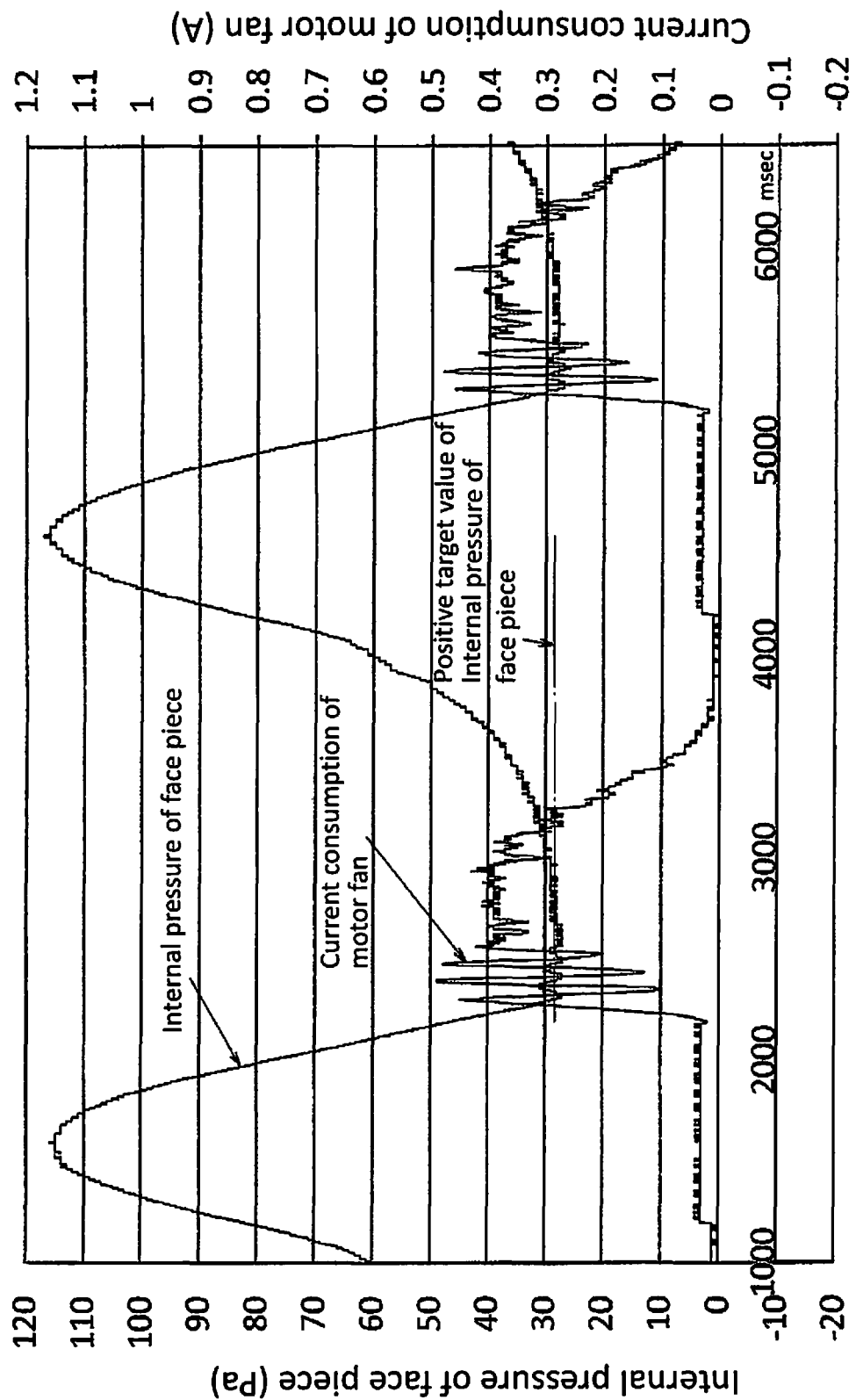

BREATHING APPARATUS PROVIDED WITH A BREATH-SYNCHRONIZED MOTOR FAN

This is a National Phase Application in the United States of International Patent Application No. PCT/JP2017/015168 filed Apr. 13, 2017, which claims priority on Japanese Patent Application No. 2016-146838, filed Jul. 26, 2016. The entire disclosures of the above patent applications are hereby incorporated by reference.

TECHNICAL FIELD

The present invention relates to a breathing apparatus provided with a breath-synchronized motor fan.

BACKGROUND ART

Each of Patent Documents No. 1 and No. 2 teaches a breathing apparatus provided with a breath-synchronized motor fan comprising a face piece for covering a part of or all of a face of a user, an inhale valve and an exhale valve attached to the face piece, a motor fan for supplying internal space of the face piece with external air through the inhale valve, a filter for cleaning the external air to be sucked into the motor fan, a breath monitoring apparatus provided with a membrane member deforming in accordance with fluctuation of internal pressure of the face piece and a sensor for detecting the deformation of the membrane member, and a controller for controlling operation of the motor fan synchronously with breathing of the user in accordance with a detection signal from the breath monitoring apparatus, wherein the controller applies current to the motor fan at the time of inhalation so as to keep the internal pressure of the face piece at a predetermined positive target value, and stops current application to the motor fan so as to stop the motor fan at the time of exhalation.

The breathing apparatus of each of Patent Documents No. 1 and No. 2 has advantages, such as that electric power consumption of the motor fan is saved because the motor fan is stopped at the time of exhalation, and that inhalation becomes easy and entry of contaminated external air into the internal space of the face piece is prevented at the time of inhalation because the motor fan operates so as to keep the internal pressure of the face piece at a predetermined positive value at the time of inhalation.

Prior Art Document

Patent Document

Patent Document No. 1: Japanese Patent Laid-Open Publication No. 2009-136521

Patent Document No. 2: Japanese Patent Laid-Open Publication No. 2013-220280

DISCLOSURE OF INVENTION

Problem to be Solved

The breathing apparatus of Patent Document No. 2 was fitted on a breathing simulator, the motor fan was operated synchronously with the breathing operation of the simulator and time-dependent changes of internal pressure of the face piece and current consumption of the motor fan were measured. Results of the measurements are shown in FIG. 1.

As can be seen from FIG. 1, in the conventional breathing apparatus provided with a breath-synchronized motor fan disclosed by Patent Document No. 2, the controller judges that the breathing is in an exhale state and stops application of current to the motor fan at the time when internal pressure of the face piece detected by the breath monitoring apparatus is higher than a predetermined positive value. At the time when the internal pressure of the face piece decreases from the peak value to the predetermined value, the controller judges that inhale started and starts application of current to the motor fan so as to keep the internal pressure of the face piece at a predetermined positive target value. The controller carries out feedback control of current application to the motor fan in accordance with the internal pressure of the face piece detected by the breath monitoring apparatus so as to keep the internal pressure of the face piece at the predetermined positive target value at the time of inhalation.

When current application to the motor fan starts, rotation speed of the motor fan that has been idle is increased at a stretch from zero to a value near a predetermined target speed while overcoming maximum static friction resistance. Thus, as can be seen from FIG. 1, large amount of current is applied to the motor fan. Repeated application of large amount of current to a motor coil of the motor fan causes aging deterioration of the motor of the motor fan.

When the rotation speed of the motor fan that has been idle is increased from zero, response of the motor fan to applied current is delayed under the effect of the maximum static friction resistance, and increase of rotation speed of the motor fan is delayed despite that inhalation already started. As a result, as can be seen from FIG. 1, an unfavorable situation occurs wherein the internal pressure of the face piece becomes far below the predetermined positive target value immediately after start of current application to the motor fan. The positive target value is preferably set at as low as possible from the viewpoint of saving of electric power consumption. However, considering the fact that the internal pressure of the face piece becomes far below the predetermined positive target value immediately after start of current application to the motor fan, the positive target value cannot but be set at a fairly high value. Thus, saving of electric power consumption becomes difficult.

Therefore, an object of the present invention is to provide a breathing apparatus provided with a breath-synchronized motor fan comprising a face piece for covering a part of or all of a face of a user, an inhale valve and an exhale valve attached to the face piece, a motor fan for supplying internal space of the face piece with external air through the inhale valve, a filter for cleaning the external air to be sucked into the motor fan, a breath monitoring apparatus provided with a membrane member deforming in accordance with fluctuation of internal pressure of the face piece and a sensor for detecting the deformation of the membrane member, and a controller for controlling operation of the motor fan synchronously with breathing of the user in accordance with a detection signal from the breath monitoring apparatus, wherein the controller applies current to the motor fan at the time of inhalation so as to keep the internal pressure of the face piece at a predetermined positive target value, and stops current application to the motor fan so as to stop the motor fan at the time of exhalation, and wherein current for keeping internal pressure of the face piece at a predetermined positive target value at the time of inhale is not applied to the motor fan in a large amount at the start of current application to the motor fan, and the internal pressure of the face piece is prevented from becoming far below the predetermined positive target value immediately after start of current application to the motor fan so as to keep the internal pressure of the face piece at a predetermined positive target value at the time of inhale.

Means for Achieving the Object

In accordance with the present invention, there is provided a breathing apparatus provided with a breath-synchronized motor fan comprising a face piece for covering a part of or all of a face of a user, an inhale valve and an exhale valve attached to the face piece, a motor fan for supplying internal space of the face piece with external air through the inhale valve, a filter for cleaning the external air to be sucked into the motor fan, a breath monitoring apparatus provided with a membrane member deforming in accordance with fluctuation of internal pressure of the face piece and a sensor for detecting the deformation of the membrane member, and a controller for controlling operation of the motor fan synchronously with breathing of the user in accordance with a detection signal from the breath monitoring apparatus, wherein the controller applies current to the motor fan at the time of inhalation so as to keep the internal pressure of the face piece at a predetermined positive target value, and stops current application to the motor fan so as to stop the motor fan at the time of exhalation, and wherein the controller applies micro-current to the motor fan so as to rotate the motor fan at extremely low speed from the middle of exhalation to inhalation.

In the present invention, differently from the case wherein rotation speed of the motor fan that has been idle is increased at a stretch from zero to a value near a predetermined target speed while overcoming maximum static friction resistance, rotation speed of the motor fan, which is already rotating at an extremely low speed, has only to be increased at a stretch from the extremely low speed to a value near a predetermined target speed while overcoming dynamical friction resistance. Therefore, amount of current applied to the motor fan does not become large. As a result, current for keeping internal pressure of the face piece at a predetermined positive target value at the time of inhale is not applied to the motor fan in a large amount at the start of current application to the motor fan. When the motor fan is started at the middle of exhalation, large amount of current is not applied to the motor fan because rotation speed is increased from zero to only extremely low speed. Furthermore, differently from the case wherein rotation speed of the motor fan that has been idling is increased from zero while overcoming maximum static friction resistance, rotation speed of the motor fan, which is already rotating at an extremely low speed, has only to be increased from the extremely low speed while overcoming dynamical friction resistance. Therefore, response of the motor fan to applied current is little delayed, and internal pressure of the face piece is prevented from becoming far below the predetermined positive target value immediately after start of current application to the motor fan so as to keep the internal pressure of the face piece at predetermined positive target value at the time of inhale.

BRIEF DESCRIPTION OF THE DRAWINGS

FIG. 3 is a diagram showing time-dependent changes of internal pressure of a face piece and current consumption of a motor fan of a breathing apparatus provided with a breath-synchronized motor fan in accordance with a preferred embodiment of the present invention.

MODES FOR CARRYING OUT THE INVENTION

A breathing apparatus provided with a breath-synchronized motor fan in accordance with a preferred embodiment of the present invention will be described.

Figure 1:
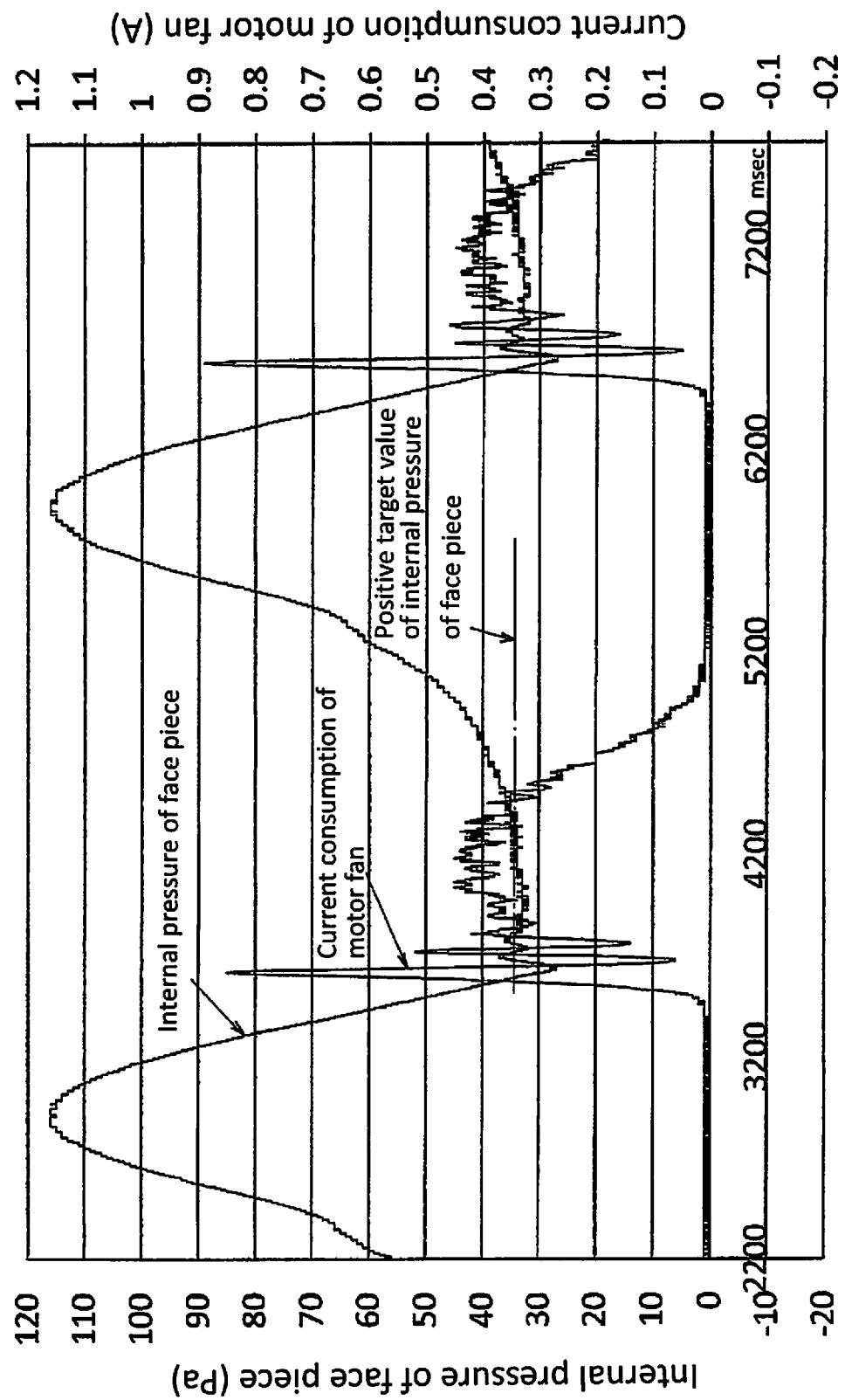
FIG. 1 is a diagram showing time-dependent changes of internal pressure of a face piece and current consumption of a motor fan of a conventional breathing apparatus provided with a breath-synchronized motor fan.
Figure 2:
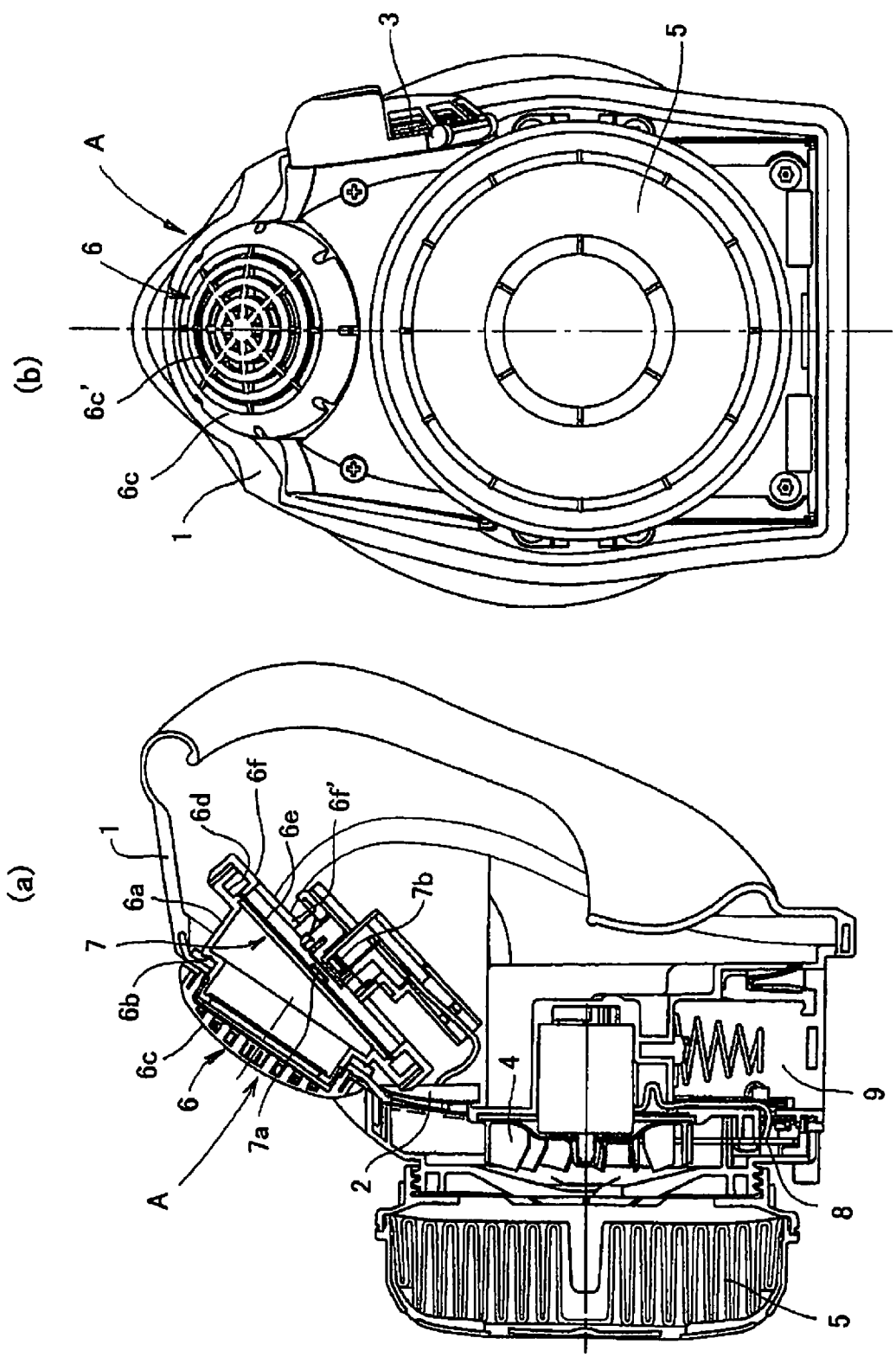
FIG. 2 is a set of structural views of a breathing apparatus provided with a breath-synchronized motor fan in accordance with a preferred embodiment of the present invention, in which (a) is a side sectional view and (b) is a front view.

As shown in FIG. 2, a breathing apparatus A provided with a breath-synchronized motor fan comprises a bowl-shaped half face piece 1 for covering the nose and the mouth of a user, an inhale valve 2 and an exhale valve 3 which are formed as reed valves and provided on the face piece 1, a motor fan 4 located upstream of the inhale valve 2 in relation to the inhale air flow so as to supply external air into the face piece 1 through the inhale valve 2, a filter 5 located upstream of the motor fan 4 in relation to the inhale air flow so as to clean the external air sucked into the motor fan 4, and a voice conductor 6.

The voice conductor 6 comprises a cylindrical body 6a provided with a small diameter portion, a middle diameter portion and a large diameter portion and is fitted in an opening formed in the face piece 1 from the inside of the face piece at the small diameter portion, a cup-shaped cover 6c threadedly engaged with an end portion of the small diameter portion projecting outside the face piece from the outside of the face piece so as to cooperate with an annular step part 6b between the small diameter portion and the middle diameter portion of the cylindrical body 6a, thereby clamping a part of the face piece 1 surrounding the opening and fixing the cylindrical body 6a to the face piece 1, a circular vibration membrane 6e abutting an annular step part 6d between the middle diameter portion and the large diameter portion of the cylindrical body 6a at outer peripheral portion from the inside of the face piece, and a circular ring-shaped frame body 6f threadedly engaged with the large diameter portion of the cylindrical body 6a so as to cooperate with the annular step part 6d, thereby clamping the outer peripheral portion of the vibration membrane 6e and fixing the vibration membrane 6e to the cylindrical body 6a. The cover 6c is provided with a plurality of holes 6c'. The frame body 6f is provided with an arm 6f' passing through the center of the circular ring and connecting two points on the circumference of the circular ring which oppose each other with the center of the circular ring between them.

The inhale valve 2, the motor fan 4, the filter 5 and the voice conductor 6 are attached to the front surface of the face piece 1. The exhale valve 3 is attached to a side surface of the face piece 1.

The breathing apparatus A comprises a breath monitoring apparatus 7. The breath monitoring apparatus 7 comprises a magnet 7a attached to the center of the vibration membrane 6e provided for the voice conductor 6, and a Hall element 7b attached to the longitudinal middle of the arm 6f' of the voice conductor 6 and opposing the magnet 7a at a predetermined distance.

The Hall element 7b and the motor fan 4 are connected to a controller 8 located near the motor fan 4, and the controller 8 is connected to a battery, which is not shown in the Figures, fitted in a battery receiving compartment 9 located near the motor fan 4.

The aforementioned structure of the breathing apparatus A is the same that of the breathing apparatus provided with a breath-synchronized motor fan disclosed in the prior art document No. 2. However, operation control of the motor fan 4 is partially different from that of the breathing apparatus provided with a breath-synchronized motor fan disclosed in the prior art document No. 2.

Operation of the breathing apparatus A will be described.

When the breathing apparatus A is not in use, the internal pressure (gage pressure) of the face piece 1 is zero, so that the internal pressure and the external pressure applied to the vibration membrane 6e balance with each other. In the following description, the internal pressure of the face piece 1 is gage pressure. When the vibration membrane 6e is in the initial condition, wherein the vibration membrane 6e extends approximately flat, the distance between the magnet 7a and the Hall element 7b becomes the initial value, and the magnetic flux density detected by the Hall element 7b also becomes the initial value.

When the internal pressure of the face piece 1 is positive, the vibration membrane 6e swells outward of the face piece 1. When the internal pressure of the face piece 1 is negative, the vibration membrane 6e subsides toward the internal space of the face piece 1.

When the breathing apparatus A is used, the battery, which is not shown in the Figures, is installed in the battery storage compartment 9 so as to start the controller 8. The face piece 1 is put on the head of the user so as to cover a part of the face of the user including the nose and mouth. The annular periphery of the face piece 1 tightly abuts the face of the user so as to prevent external air from flowing into the face piece through the abutting portion between the annular periphery of the face piece and the face of the user.

As the user exhales and inhales, the internal pressure of the face piece 1 increases and decreases, pressure difference is generated between the internal pressure and the external pressure applied to the vibration membrane 6e, the vibration membrane 6e deforms from the initial condition, and the distance between the magnet 7a and the Hall element 7b changes from the initial value. The Hall element 7b detects the change of the magnetic flux density from the initial value caused by the aforementioned change of the distance so as to send a detection signal to the controller 8. The controller 8 recognizes that the breathing apparatus A was put on the head of the user when the magnetic flux density received from the Hall element 7b changes beyond a predetermined value from the initial value, and starts control of the motor fan 4.

The controller 8 controls the rotation speed of the motor fan 4 based on the detection signal from the Hall element 7b so that the internal pressure of the face piece 1 becomes predetermined positive target value and the vibration membrane 6e lies more outside the face piece 1 by predetermined distance after deflection than in the initial condition.

At the time of exhale, the internal pressure of the face piece 1 increases, the deflection of the vibration membrane 6e outward of the face piece 1 increases, the distance between the magnet 7a and the Hall element 7b increases, and the magnetic flux density detected by the Hall element 7b decreases. When the increment of the aforementioned distance from the initial value exceeds a predetermined value and the decrement of the magnetic flux density detected by the Hall element 7b from the initial value exceeds a predetermined value, in other words, when internal pressure of the face piece 1 exceeds a predetermined value, the controller 8 recognizes that the breathing is in exhaling condition and responds by stopping current application to the motor fan 4, thereby stopping the motor fan 4. As a result, electric power consumption is saved, exhaustion of the battery is minimized, and clogging of the filter 5 is inhibited. At the time of exhale, the inhale valve 2 closes and the exhale valve 3 opens. The exhaled air is exhausted into the external environment through the exhale valve 3.

When the user of the breathing apparatus A speaks aloud, the vibration membrane 6e of the voice conductor 6 vibrates. Deflection of the vibration membrane 6e outward and inward of the face piece 1 when the user of the breathing apparatus A speaks aloud is smaller by far than deflection of the vibration membrane 6e outward and inward of the face piece 1 when the user breaths. Therefore, even if the user speaks aloud, it does not affect the operation of the motor fan 4.

At the time of inhale, the internal pressure of the face piece 1 decreases, the deflection of the vibration membrane 6e outward of the face piece 1 decreases, the distance between the magnet 7a and the Hall element 7b decreases, and the magnetic flux density detected by the Hall element 7b increases. When the increment of the aforementioned distance from the initial value becomes equal to or less than the predetermined value and the decrement of the magnetic flux density detected by the Hall element 7b from the initial value becomes equal to or less than the predetermined value, in other words, when internal pressure of the face piece 1 becomes equal to or less than the predetermined value, the controller 8 recognizes that the breathing is in inhaling condition and responds by applying current to the motor fan 4, thereby rotating the motor fan 4 and keeping the internal pressure of the face piece 1 at a predetermined positive target value. At the time of inhale, the inhale valve 2 opens and the exhale valve 3 closes. External air is passed through the filter 5 to be freed of dust, sucked into the motor fan 4, and passed into the face piece 1 through the inhale valve 2. The internal pressure of the face piece 1 is kept at the predetermined positive value due to rotation of the motor fan 4 which causes air flow into the face piece 1. Thus, the breathing of the user of the breathing apparatus becomes easy and contaminated air in the external environment is prevented from entering into the face piece 1.

When the breathing apparatus A is removed from the head of the user, the internal pressure and the external pressure applied to the vibration membrane 6e balance with each other, the vibration membrane 6e returns to the initial condition, the distance between the magnet 7a and the Hall element 7b returns to the initial value, and the magnetic flux density of the magnet 7a detected by the Hall element 7b returns to the initial value. When the magnetic flux density of the magnet 7a received from the Hall element 7b is kept at the initial value for a predetermined time, the controller 8 recognizes that the breathing apparatus A was removed from the head of the user and responds by stopping the motor fan 4.

As previously described, the controller 8 of the breathing apparatus A applies current to the motor fan 4 so as to rotate it, thereby keeping the internal pressure of the face piece at the predetermined positive target value at the time of inhalation, and stops application of current to the motor fan 4 so as to stop it at the time of exhalation. Furthermore, the controller 8 applies micro-current to the motor fan 4 so as to rotate it at extremely low speed from the middle of exhalation to inhalation.

The breathing apparatus A was fitted on a breathing simulator, the motor fan 4 was operated synchronously with the breathing operation of the simulator and time-dependent changes of internal pressure of the face piece and current consumption of the motor fan were measured. Results of the measurement are shown in FIG. 3.

Differently from the conventional case wherein rotation speed of the motor fan that has been idle is increased at a stretch from zero to a value near a predetermined target value while overcoming maximum static friction resistance, in the breathing apparatus A, rotation speed of the motor fan 4, which is already rotating at extremely low speed, has only to be increased at a stretch from the extremely low speed to a value near a predetermined target value while overcoming dynamical friction resistance. Therefore, amount of current applied to the motor fan 4 does not become large. As a result, as can be seen from FIG. 3, current for keeping internal pressure of the face piece at the predetermined positive target value is not applied to the motor fan 4 in a large amount at the start of current application to the motor fan.

When the motor fan 4 is started at the middle of exhalation, large amount of current is not applied to the motor fan 4 because rotation speed is increased from zero to only extremely low speed.

Furthermore, differently from the conventional case wherein rotation speed of the motor fan that has been idle is increased from zero while overcoming maximum static friction resistance, in the breathing apparatus A, rotation speed of the motor fan 4, which is already rotating at extremely low speed, has only to be increased from the extremely low speed while overcoming dynamical friction resistance. Therefore, response of the motor fan 4 to applied current is little delayed, and, as can be seen from FIG. 3, internal pressure of the face piece is prevented from becoming far below the predetermined positive target value immediately after start of current application to the motor fan 4 so as to keep the internal pressure of the face piece at predetermined positive target value at the time of inhale. As a result, the aforesaid predetermined positive target value can be set within a proper range at a value lower than that in the conventional breathing apparatus. Thus, electric power consumption is saved.

Electric power consumption increment due to the micro-current applied to the motor fan 4 from the middle of exhalation to inhalation offsets electric power consumption decrement due to the fact that current for keeping internal pressure of the face piece at the predetermined positive target value is not applied to the motor fan 4 in a large amount at the start of current application to the motor fan. Therefore, the aforesaid micro-current application does not cause increase of electric power consumption.

In the aforementioned embodiment, 7a is a magnet and 7b is a Hall element, and displacement of the vibration membrane 6e is detected by the magnet 7a and the Hall element 7b. It is possible to make 7a a reflector and 7b an optical sensor made of a light emitting member and a light receiving member, so as to detect displacement of the vibration membrane 6e by the reflector 7a and the optical sensor 7b.

The face piece 1 can be a full face type face piece for covering the whole face.

It is possible to use another type of membrane member in place of the vibration membrane 6e of the voice conductor 6 for constituting the breath monitoring apparatus 7.

INDUSTRIAL APPLICABILITY

The present invention can be widely used for breathing apparatuses provided with a breath-synchronized motor fan

BRIEF DESCRIPTION OF THE REFERENCE NUMERALS

A Breathing apparatus
1 Face piece
2 Inhale valve
3 Exhale valve
4 Motor fan
5 Filter
6 Voice conductor
6e Vibration membrane
7 Breath monitoring apparatus
7a Magnet
7b Hall element
8 Controller

The invention claimed is:
1. A breathing apparatus comprising a face piece for covering a part of or all of a face of a user, an inhale valve and an exhale valve attached to the face piece, a motor fan directly attached to the face piece for supplying internal space of the face piece with external air through the inhale valve, a filter for cleaning the external air to be sucked into the motor fan, a breath monitoring apparatus provided with a membrane member deforming in accordance with fluctuation of internal pressure of the face piece and a sensor for detecting the deformation of the membrane member, and a controller for controlling operation of the motor fan synchronously with breathing of the user in accordance with a detection signal from the breath monitoring apparatus, wherein the controller is configured to apply current to the motor fan at the time of inhalation so as to keep the internal pressure of the face piece at a predetermined positive target value, and stop current application to the motor fan so as to stop the motor fan at the time of exhalation, and wherein the controller is further configured to start a current application to the motor fan after start of the exhalation and before internal pressure of the face piece reaches maximum exhalation pressure and continue the current application to the motor fan to inhalation.

* * * * *